United States Patent [19]

Tsoucalas

[11] Patent Number: 5,084,427

[45] Date of Patent: Jan. 28, 1992

[54] AQUEOUS SUSPENSIONS OF ALUMINOSILICATE MOLECULAR SIEVES

[75] Inventor: Michael C. Tsoucalas, Bergenfield, N.J.

[73] Assignee: UOP, Des Plaines, Ill.

[21] Appl. No.: 600,782

[22] Filed: Oct. 22, 1990

[51] Int. Cl.$^5$ .......................... B01J 20/18; B01J 20/22
[52] U.S. Cl. .......................................... 502/62; 502/68
[58] Field of Search .................................... 502/62, 68

[56] References Cited

U.S. PATENT DOCUMENTS

| | | | |
|---|---|---|---|
| 3,203,903 | 8/1965 | Van Olphen | 502/62 |
| 3,781,225 | 12/1973 | Schwartz | 502/62 |
| 4,138,363 | 2/1979 | Hertzenberg et al. | 502/62 |

FOREIGN PATENT DOCUMENTS

| | | | |
|---|---|---|---|
| 61614 | 4/1982 | Japan | 502/62 |
| 61617 | 4/1982 | Japan | 502/62 |
| 1200853 | 9/1986 | Japan | 502/62 |
| 2153116 | 7/1987 | Japan | 502/62 |

Primary Examiner—Carl F. Dees
Attorney, Agent, or Firm—Thomas K. McBride; Richard G. Miller

[57] ABSTRACT

Stable aqueous suspensions of crystalline aluminosilicate molecular sieve particles, particularly hydrophobic crystalline siliceous molecular sieves, are provided in compositions having a consistency ranging from thin lotions to semi-solid "stick" formulations. The aqueous suspensions are maintained using hydrophilic colloids, particularly a mixture of a colloidal magnesium silicate having the structure of smectite and an alkali metal salt of the carboxymethoxy ether of cellulose.

11 Claims, No Drawings

AQUEOUS SUSPENSIONS OF ALUMINOSILICATE MOLECULAR SIEVES

Field of the Invention

The present invention relates in general to aqueous suspensions of crystalline aluminosilicate molecular sieves, preferably hydrophobic high-silica molecular sieve particles and, more particularly, to aqueous creams and lotions in which the molecular sieve particles are suspended with hydrophilic colloids. As a specific embodiment of the invention there is provided an aqueous suspension of hydrophobic zeolitic molecular sieve particles suitable for topical application to sources of objectionable odors for elimination thereof.

The methods for suspending solid particles in liquid media have been investigated for a very long time. In general the solid particles are more dense than the suspension medium so that gravitational forces tend to cause settling and accumulation of the particles at the bottom of the container. Complex interactions between the particle and the medium, moreover, result in non-uniform electrical charge distributions which can cause the agglomeration or "clumping" of particles with adverse effects upon the homogeneity of the overall composition. The ability to maintain a homogeneous state for long periods is usually a very important property for liquid suspensions of solids. Because of the diversity of physical and chemical properties of both the solid particles to be suspended and the suspension media, the suspension art is a relatively unpredictable one despite the considerable attention it has received and the existence of some general guidelines. For example, the difficulty of preparing a stable homogeneous liquid detergent containing a water-insoluble builder or zeolitic ion-exchanger is reported in U.S. Pat. No. 4,409,136, issued Oct. 11, 1983, to B. Cheng.

In addition to the property of being homogeneous, the rheology of the composition of solid particles suspended in a liquid medium is frequently very important to facilitate accurate dispensing and topical application. The ease of application and the feel of the composition on the skin is especially important in cosmetic or therapeutic compositions, as indicated in U.S. Pat. No. 4,362,715, issued Dec. 7, 1982, to Strianse et al.

It is frequently the case that it is desired to impart solid particles to surfaces wherein the principal goal is an even distribution of the particles adhered to the surface. For example, in U.S. Pat. No. 4,826,497, issued May 2, 1989, to B. K. Marcus et al, there are disclosed a variety of fibrous adsorbent articles such as disposable diapers, wound dressings, shoe inserts and the like in which an essential aspect is the retention on the fibers of the articles of particle of crystalline siliceous molecular sieves which function as odor eliminators. It is important to the efficient use of these articles that the molecular sieve particles are evenly distributed in an exposed manner on the fibers forming the article and that they are not readily dislodged and become separated from the article. An effective means of incorporating the particles to such articles is by the application of a liquid containing the particles, preferably an aqueous suspension, with the subsequent removal of the liquid medium. For commercial manufacturing processes, it is vital that the suspension of molecular sieve particles be homogeneous, have the proper rheological properties and maintain the particles in a highly dispersed state.

SUMMARY OF THE INVENTION

We have now discovered novel compositions which are suitable for the topical application of crystalline molecular sieve particles, preferably hydrophobic siliceous molecular sieve particles, to surfaces, including the skin and fibrous articles, which are stable suspensions of the particles in aqueous or hydroalcoholic vehicles. These compositions, which can vary in consistency from thick creams to thin lotions, comprise, in addition to the particles and the aqueous or hydroalcoholic medium, a colloidal magnesium silicate, preferably a magnesium aluminum silicate of the smectite type, and an alkali metal salt of the carboxymethoxy ether of cellulose.

DETAILED DESCRIPTION OF THE INVENTION

The molecular sieves suitably employed in the compositions of the present invention include any of the crystalline aluminosilicates well known in the art either as naturally occurring minerals or as synthetic species such as zeolite X, zeolite A, ZSM-5 or zeolite Omega. Preferably, however, the molecular sieves are hydrophobic crystalline siliceous molecular sieves in which at least about 90, and preferably at least 95, percent of the framework tetrahedral oxide units are $SiO_2$ tetrahedra and which have a sorptive capacity for water at 25° C. and 4.6 torr of less than about 10 weight percent, preferably less than about 6 weight percent. In the case of aluminosilicate molecular sieves, the framework $SiO_2/Al_2O_3$ molar ratio is at least 18 and is preferably at least 35. Molecular sieve zeolites having framework molar $Si/Al2$ ratios of from 200 to 500 are particularly suitable. Many of the synthetic zeolites prepared using organic templating agents are readily produced in a highly siliceous form. In many instances the reaction mixtures can be especially free of aluminum-containing reagents. These zeolites are markedly organophilic and include ZSM-5 (U.S. Pat. No. 3,702,886); ZSM-11 (U.S. Pat. No. 3,709,979); ZSM-35 (U.S. Pat. No. 4,016,245); ZSM-23 (U.S. Pat. No. 4,076,842); and ZSM-38 (U.S. Pat. No. 4,046,859) to name only a few. It has been found that the silica molecular sieves known as silicalite and F-silicalite are particularly suitable for use in the present invention and are thus preferred. These materials are disclosed in U.S. Pat. Nos. 4,061,724 and 4,073,865, respectively. To the extent the aforesaid siliceous sieves are synthesized to have $SiO_2/Al_2O_3$ ratios greater than 35, they are frequently suitable for use in the present compositions without any additional treatment to increase their degree of hydro- phobicity. Molecular sieves which cannot be directly synthesized to have both sufficiently high Si/Al and/or degree of hydrophobicity ratios can be subjected to dealumination techniques, fluorine treatments and the like, which result in organophilic zeolite products. High-temperature steaming procedures for treating zeolite Y which result in hydrophobic product forms are reported by P. K. Maher et al, "Molecular Sieve Zeolites," Advan. Chem. Ser. 101, Americal Chemical Society, Washington, D. C., 1971, p. 266. A more recently reported procedure applicable to zeolite species generally involves dealumination and the substitution of silicon into the dealuminated lattice site. This process is disclosed in U.S. Pat. No. 4,503,023, issued Mar. 5, 1985 to Skeels et al. Halogen or halide compound treatments for zeolites to increase their hydrophobicity are disclosed in U.S. Pat. Nos. 4,569,833 and 4,297,335.

In the case of the aluminosilicates or silica polymorphs produced using large organic templating ions such as tetraalkylammonium ions, it is frequently necessary to remove charge balancing organic ions and any occluded templating material in order to permit their use in adsorption processes.

It should be pointed out that with respect to the hydrophobic aluminosilicates it is the framework $SiO_2/Al_2O_3$ ratio which is important. This is not necessarily the same ratio as would be indicated by conventional wet chemical analysis. Especially is this the case when dealumination has been accomplished by high temperature steaming treatments wherein aluminum-containing tetrahedral units of the zeolite are destroyed, but the aluminum values remain, at least in part, in the zeolite crystals. For such zeolite products resort must be had to other analytical methods such as X-ray and NMR. One such steam-treated zeolite Y composition, known in the art as LZ-10, has been found to be particularly useful in the compositions of the present process, especially when utilized in combination with the silica polymorph silicalite. The process for preparing LZ-10 is described in detail in U.S. Pat. No. 4,331,694. When applied to the sequestration of organic odors, a benefit appears to be obtained by such a combination of molecular sieves in all proportions, but each type of adsorbent is preferably present in an amount of at least 10 percent based on the total weight of the two adsorbents (hydrated weight basis).

As synthesized the molecular sieve particles have, in general, sizes of about 1.5 to about 6.0 micrometers. The particles are most frequently agglomerates having sizes in the rang of 10 to about 20 micrometers. Molecular sieve particles in this range, i.e., 10 to 20 micrometers, are all suitably utilized in forming the present compositions. It is preferred, however, that the particles are within the size range of 1.5 to 6.0 micrometers. If it is necessary to reduce the molecular sieve particle size, the grinding techniques well known in the art are suitably employed.

The hydrophilic colloid system used to suspend the molecular sieve particles comprises, in addition to water and/or alcohol, a colloidal magnesium aluminum silicate and alkali metal carboxymethyl cellulose. The colloidal magnesium silicate is refined from natural minerals commonly called smectite or montmorillonite clays. These clay minerals are characterized by an expanding lattice structure which swells when heated and dispersed in water. Another and similar clay is called hectorite or macaloid. This material is a mined smectite clay with a sodium magnesium-fluoro-litho-silicate structure. The magnesium, lithium and fluorine are inaccessibly located within the lattice structure and are, therefore, not water soluble or exchangeable. A synthetic magnesium silicate, known as laponite having properties similar to natural smectites, is also known. This silicate contains exchangeable lithium and calcium cations in place of the aluminum present in natural smectite clays. As used herein, these clays, both synthetic and naturally occurring, are identified by the term magnesium silicates of the smectite type or, alternatively, as magnesium silicates having the smectite structure.

In preparing the colloidal dispersion of the magnesium silicates of the smectite type for use in preparing the compositions of the present invention, the starting compositions are hydrated in such a manner that the cations diffuse away from the charged layered platelets outside the lattice structure. As hydration continues, the clay swells until ultimately the platelets separate completely and form a clear colloidal dispersion of platelets and cations in solution. The platelets carry a surface negative charge and a small positive charge on their edges due to the disruption of the original crystal lattice. In dilute solution, the surface negative charges are much larger than the positive charges on the platelet edges. Consequently, repulsion occurs between particles and no thickening of the system occurs. As the ionic content of the aqueous medium increases, either due to the addition of electrolyte or increasing clay concentration, the surface charge on the particles is reduced and the dominant force becomes the surface-to-edge attraction. The result is the formation of a gel. The ionic bonds between particle surface and particle edge are easily broken and reformed, however, giving rise to a thixotropic system with low viscosity under shear and a high yield value. Care must be taken to avoid an undue increase in the electrolyte content whereby the surface negative charge is overcome and the platelets bind together with resultant flocculation. A suitable colloidal magnesium aluminum silicate is available commercially from R. T. Vanderbilt Company under the registered trademark VEEGUM.

The third essential ingredient of the present compositions, an alkali metal salt of the carboxymethyl ether of cellulose, (CMC), is an anionic water-soluble polymer derived from cellulose by the reaction of alkali metal chloracetate with alkali cellulose. It is classified as an anionic polyelectrolyte and is commercially available predominantly as the sodium salt. The properties of CMC can vary considerably, the principal determinants being the degree of substitution (DS) and the degree of polymerization (DP) or chain length. The DS is defined as the average number of carboxymethyl groups introduced, i.e., substituted for hydroxyl groups per anhydroglucose unit in the cellulose. The DP is determined by the chain length of the starting cellulose which can be as high as 5000. The DP is reflected in the viscosity of the CMC solution and as the DP increases the viscosity increases. CMC is commercially available in viscosities from about 3000 cP in 1% solution to 17 cP in 2% solution, corresponding to a DP range of from about 1000 to 200. In the compositions of the present invention the DS should be in the range of 0.38 to about 1.45, preferably in the range of 0.65 to 0.90.

In addition to the aforesaid three essential constituents of the vehicle in the present compositions, a number of other materials can be added to provide cosmetic and/or formulation functionality. These include propylene glycol, hexylene glycol and 1,3-butylene glycol, all of which serve to act as rheological modifiers. Colorants and pigments are suitably incorporated into the present compositions, as are fragrances which are compatible with, i.e., not eliminated by the activity of, the high-silica zeolites also present. Lower alcohols such as ethanol and isopropanol can also be included to the extent they do not cause precipitation of the CMC constituent. Fungicides, bacteriacides and medicinal or therapeutic materials can also be present.

The proportions of the essential constituents in the present compositions are not narrowly critical. Preferably the high-silica molecular sieves are present in an amount of 5 to 50 parts by weight (anhydrous weight of the molecular sieve) and more preferably from 10 to 25 parts by weight (pbw). The content of magnesium silicate of the smectite type is generally in the range of 0.45 to 2.5 pbw, preferably 1.6 to 1.8 pbw. CMC is advantageously present in an amount of 0.2 to 1.25 pbw, preferably 0.8 to 0.9 pbw. Water, exclusive of water added as a normal part of the magnesium silicate and the CMC, is preferably included in an amount of from 40 to 89 pbw, although the amount employed will depend in large measure upon the desired consistency of the product, and relative proportions of the other constituents.

We have found that the particular hydrophilic colloid system of the present composition performs two separate functions which together accomplish the effective suspension of the solid molecular sieve particles. Firstly, the zeta potential of the solid particles is lowered to a degree adequate to keep the solid particles separated in the liquid medium. Secondly, the viscosity of the medium is increased to a significant degree which aids in suspending the solid particles and preventing Stokes Law from taking effect. This dual functionality is not provided by any of the suspension agents commonly utilized in the prior art. For example, neither hydroxyethyl cellulose nor carboxypolymethylene, available commercially under the trademarks Natrosol 250MR (Aqualon Company) and Carbopol 941 (B. F. Goodrich Company), respectively, have been found by zeta potential measurements and physical stability testing in aqueous systems containing high-silica zeolite particles to be adequate in lowering the zeta potential. Their only function in such systems appears to be to increase the viscosity of the composition. On the other hand, a number of commercially available polyelectrolyte suspension aids which lower the zeta potential significantly in other dispersed phases were inadequate for that purpose in aqueous suspensions of high-silica zeolites. These include a copolymer of sodium acrylate and acrylamide (available commercially from Allied Colloids Company under the trademark Percol 726 and Percol 727); the sodium salt of a polymerized napthalene sulfonic acid and the sodium salt of a polymerized alkyl napthalene sulfonic acid (both available commercially under the trademarks Darvan No. 1 and Darvan No. 9, respectively, from R. T. Vanderbilt Company); a penta sodium salt of aminotri (methylene phosphonic acid) sold commercially by Monsanto Chemical Company under the trademark Dequest 2006; and the sodium salt of a polymeric carboxylic acid, a polyelectrolyte with an anionic charge similar to Dequest 2006, sold by Allied Colloid Company under the trademark Dispex N-40. Tests with these materials in attempts to form stable suspensions of high-silica zeolite particles showed no success because Stokes Law took effect and the molecular sieve particles settled out of the aqueous medium almost immediately. This was particularly surprising in the case of Dequest 2006. This penta sodium polyelectrolyte is known to be an effective dispersing agent designed to prevent agglomeration or coalescence of suspended solids by increasing the anionic charge on the particles to be dispersed. Unlike polyphosphates, it possesses hydrolytic stability and can maintain kaolin slurries in a deflocculated state for periods longer than polyphosphates are capable of doing. Of the aforementioned polyelectrolytes, only Percol 726 was found to be able to lower the zeta potential sufficiently to give even a temporary suspension of the molecular sieve particles. The presence, however, of hydrophobic "tails" on the Percol 726 caused a coagulation of the type resembling cottage cheese.

Further, non-surfactant type hydrophilic colloids that merely coat the molecular sieve particles were also tested, but were found not to prevent settling of the particles. These included polyvinylpyrrolidone, Gantrez AN (a trademark of GAF Chemical Company) and Resyn 28-1310 and Resyn 28-2930, both trademarks of National Starch Company. Gantrez AN is a copolymer of vinyl ether and maleic anhydride. It is a water-soluble polymeric anhydride that slowly hydrolizes in the presence of water to form the free acid. Addition of small quantities of alkali aids solution, but must be controlled since it results in dramatic increase in viscosity of the dispersed aqueous phase. PVM/MA copolymer acts as a protective colloid by adsorbing on to the surface of solids that are to be dispersed and suspended. It is available in several molecular weight ranges. The grades 119 and 169 reflect molecular weights ranging from 20,000 to 67,000. Resyn 280-1310 is a carboxylated vinyl acetate copolymer which must be neutralized from ethanol solutions to achieve water solubility. When neutralized with an amino hydroxy compound such as AMP (2-Amino-2-Methyl-1-Propanol) water solubility occurs. Coating suspended particles in hydroalcoholic vehicles with the neutralized resyn may prevent coalescence of solid particles by the process of adsorption. The resyn in this case acts as a protective colloid to prevent contact with other solid particles. Resyn 28-2930 is a terpolymer of vinylacetate, crotonic acid and neo-decanoate. As with Resyn 28-1310, ethanol solutions of this polymer must be neutralized with AMP to achieve water solubility.

The results of the zeta potential measurements are set forth in Tables I and II, infra. In making each test, samples of deionized water, containing 5 and 10 weight percent of a hydrophobic siliceous molecular sieve, respectively, was used as the control sample. The dispersing agents or suspension aids were added to slurries of the molecular sieve in deionized water using the proportions, in weight percent, indicated in the Tables. In Table I the zeta potentials were determined by acoustics and in Table II by electrophoretic mobility.

TABLE I

| SAMPLE | DISPERSING AGENT | MOL. SIEVE PARTICLES WT % | pH | ZETA POTENTIAL (MV) |
|---|---|---|---|---|
| Control | None | 10.0 | 6.0 | −42.0 |
| A | DEQUEST 2006 1.0% | 10.0 | 6.5 | −42.0 |
| B | DEQUEST 2006 2.0% | 10.0 | 6.7 | −42.0 |
| Control | None | 10.0 | 6.3 | −41.0 |
| C | DARVAN NO. 1 1.0% | 10.0 | 5.6 | −25.0 |
| D | DARVAN NO. 1 2.0% | 10.0 | 5.4 | −22.0 |
| Control | None | 10.0 | 6.3 | −42.0 |
| E | DARVAN NO. 9 1.0% | 10.0 | 5.7 | −37.0 |
| F | DARVAN NO. 9 2.0% | 10.0 | 5.6 | −35.0 |
| Control | None | 10.0 | 6.3 | −40.0 |
| G | GANTREZ 119 1.0% | 10.0 | 5.5 | −39.0 |
| H | GANTREZ 119 2.0% | 10.0 | 5.0 | −37.0 |
| Control | None | 10.0 | 6.3 | −41.0 |
| I | GANTREZ 169 1.0% | 10.0 | 5.7 | −39.0 |
| J | GANTREZ 169 2.0% | 10.0 | 5.2 | −40.0 |

TABLE II

| SAMPLE | DISPERSING AGENT | MOL. SIEVE PARTICLES WT % | pH | ZETA POTENTIAL (MV) |
| --- | --- | --- | --- | --- |
| Control | None | 5.0 | 5.9 | −26.0 |
| K | PERCOL 726 0.05% | 10.0 | 5.8 | −38.0 |
| L | DISPEX N-40 0.05% | 10.0 | 4.8 | +12.0 |
| M | VEEGUM/CMC 0.45%/0.225% | 10.0 | 5.7 | −43.0 |
| N | VEEGUM/CMC 0.90%/0.45% | 10.0 | 5.9 | −54.0 |
| O | VEEGUM/CMC 1.8%/0.9% | 10.0 | 6.2 | −52.0 |
| P | VEEGUM/CMC 1.8%/0.9% | 25.0 | 5.8 | −50.0 |
| Q | CARBOPOL 941 0.80% | 10.0 | 7.4 | −31.4 |
| R | NATROSOL 250 1.00% | 10.0 | 5.9 | −23.0 |

The compositions of the present invention are illustrated and exemplified by the following Examples.

EXAMPLES 1-5

Five compositions were prepared using (a) deionized water, (b) a mixture of equal parts by weight of crystals of silicalite and a dealuminated and stabilized form of zeolite Y, (c) a colloidal magnesium aluminum silicate, (d) sodium carboxymethyl cellulose, (e) propylene glycol, (f) hexylene glycol and (g) 1,3 butylene glycol. All five compositions contained ingredients (a) through (d), and three of the compositions each contained one of ingredients (e), (f) and (g). The colloidal magnesium aluminum silicate was a commercial product, Veegum ®. The sodium carboxymethyl cellulose (CMC) was obtained from the Aqualon Company under the brand name CMC 7L, characterized by having a DS of about .79 and a DP of about 400. The silicate crystals were prepared in accordance with the general disclosure of U.S. Pat. No. 4,061,724. The dealuminated and stabilized form of zeolite Y was prepared by steaming a low-sodium ammonium ion-exchanged zeolite Y at a temperature in excess of 750° C. to reduce its water adsorption capacity at 25° C. and 4.6 torr water vapor pressure of less than 6 weight percent and a framework $Si/Al_2$ molar ratio of greater than 18. In forming the compositions, the water ingredient was heated to a temperature of about 70° C. and combined with the colloidal magnesium aluminum silicate. The silicate was dispersed in the water by means of mechanical (propeller) agitation for a period of about 20 minutes until the silicate was fully swelled and hydrated. Thereafter the silicate dispersion was cooled to room temperature, the CMC was added and the agitation continued for at least 1 hour until a fully swelled and hydrated suspension was obtained. The molecular sieve particles were added next along with any water needed to replace water lost by evaporation and blended for at least 1 hour until a smooth dispersion was obtained. Stability results indicate that hydration of the silicate is not achieved if the CMC is first fully hydrated before addition of the silicate to the continuous phase. Inadequate hydration of the silicate tends to cause separation of the zeolite particles from the medium. In forming the three sample compositions which contain, respectively, propylene glycol, hexylene glycol and 1,3 butylene glycol, the appropriate glycol was added as the last constituent of the compositions. Upon addition of the glycol, the mixture was blended until a smooth dispersion was obtained, taking care not to aerate the dispersion. The chemical compositions of the five dispersions are shown in Table III below in terms of weight percent of the individual constituents.

TABLE III

| INGREDIENTS | SAMPLE | | | | |
| --- | --- | --- | --- | --- | --- |
|  | 1 | 2 | 3 | 4 | 5 |
| MgAl Silicate | 1.8% | 1.8% | 1.8% | 1.8% | 1.8% |
| CMC | 0.9 | 0.9 | 0.9 | 0.9 | 0.9 |
| Molecular Sieve Particles | 10.0 | 25.0 | 10.0 | 10.0 | 10.0 |
| Water, Deionized | 87.3 | 72.3 | 82.3 | 82.3 | 82.3 |
| Propylene Glycol | — | — | 5.0 | — | — |
| Hexylene Glycol | — | — | — | 5.0 | — |
| 1,3 Butylene Glycol | — | — | — | — | 5.0 |

The compositions were analyzed for pH and viscosity (Brookfield) promptly after their preparation. A small portion of each composition was divided between two vials. The bulk samples and one of the vial samples were stored for one month at ambient room temperature and the other vial sample was held for one month at 50° C. Following the storage period the pH and the viscosity of the bulk samples were again determined and the vial samples examined by sight and touch for appearance and consistency. The results are set forth in Table VI below.

COMPARISON EXAMPLES 6-13

Using essentially the same formulation procedure as in Examples 1-5, supra, except that the water constituent was at all times at ambient room temperature, a commonly used suspension aid, namely, a hydroxyethyl ether of cellulose obtained from the Aqualon Company under the trademark Natrosol 250MR, was substituted for the CMC and the magnesium aluminum silicate of Examples 1-5 to prepare Comparison Examples 6-13. The formulations are set forth in Table IV below in terms of weight percent of each constituent.

TABLE IV

| INGREDIENTS | SAMPLE | | | | | | | |
| --- | --- | --- | --- | --- | --- | --- | --- | --- |
|  | 6 | 7 | 8 | 9 | 10 | 11 | 12 | 13 |
| NATROSOL 250 MR | 1.0% | 1.0% | 1.0% | 1.0% | 1.0% | 1.0% | 1.0% | 1.0% |
| MOL. SIEVE PARTICLES | 10.0 | 25.0 | 50.0 | 40.0 | 25.0 | 10.0 | 10.0 | 10.0 |
| WATER, DEIONIZED | 89.0 | 74.0 | 44.0 | 54.0 | 69.0 | 84.0 | 84.0 | 84.0 |
| PROPYLENE GLYCOL | — | — | — | — | — | — | — | 5.0 |
| HEXYLENE GLYCOL | — | — | 5.0 | 5.0 | 5.0 | 5.0 | — | — |
| 1,3 BUTYLENE GLYCOL | — | — | — | — | — | — | 5.0 | — |

The formulations of Examples 6-13 were analyzed for pH and viscosity and stored in bulk and vial samples (except for samples 8, 9 and 10) for one month in the same manner as Samples 1-5. The analytical results for the samples both before and after storage are shown in Table VI, below.

COMPARATIVE EXAMPLES 14-17 analytical results before and after storage are set forth in Table VI below.

TABLE VI

| Sample No. | Bulk Samples | | | | Vial Samples | |
|---|---|---|---|---|---|---|
| | Initial pH | Final pH | Initial Viscosity (cps) | Final Viscosity (cps) | @ Room Temperature | @ 50° C. |
| 1 | 5.96 | 6.24 | 104 | 594 | No change, fluid lotion | Viscous fluid lotion, no separation |
| 2 | 5.51 | 5.83 | 2,120 | 7,740 | Thick fluid cream | Dry, non-fluid cream* |
| 3 | 6.43 | 6.57 | 183 | 357 | No change, fluid lotion | Viscous fluid lotion, no separation |
| 4 | 6.67 | 6.73 | 140 | 263 | " | " |
| 5 | 6.52 | 6.61 | 150 | 340 | " | " |
| 6 | 5.59 | 5.87 | 720 | 875 | 95% liq. separation after 2 wks. does not resuspend. | 95% liquid separation after 1 week. does not resuspend. |
| 7 | 5.13 | 5.38 | 3,120 | 3,270 | No change, fluid lotion | No change, fluid lotion |
| 8 | 5.19 | 5.41 | 10,400 | 10,940 | — | — |
| 9 | 5.12 | 5.15 | 13,520 | 14,900 | — | — |
| 10 | 5.20 | 5.33 | 3,852 | 4,600 | — | — |
| 11 | 5.58 | 6.41 | 1,875 | 1,860 | No change, fluid lotion | Fluid lotion, slight sedimentation, resuspends. |
| 12 | 5.44 | 6.33 | 1,725 | 1,800 | No change, fluid lotion | " |
| 13 | 5.25 | 6.39 | 1,700 | 1,865 | " | " |
| 14 | 7.42 | 7.83 | 4,040 | 5,440 | — | — |
| 15 | 6.54 | 7.07 | 1,200 | 1,720 | Gross separation within 4 days, resuspendable | Gross separation within 4 days, resuspendable |
| 16 | 7.02 | 7.10 | 1,464 | 1,176 | Liquid separation @ 24 hrs., resuspendable | Liquid separation @ 24 hrs., resuspendable |
| 17 | 7.72 | 7.75 | 1,440 | 1,530 | — | — |

*Not suitable as a cream. Has "stick" consistency

Four formulations of aqueous suspensions of the same molecular sieve particles as in Examples 1-13 were prepared using the well-known carboxypolymethylene-type suspending aid instead of the CMC and magnesium aluminum silicate system of the present invention. The specific suspension aid employed was Carbopol 941 obtained from B. F. Goodrich Company. The formulation procedure consisted of the following five steps:

(a) Heat water to 65-70° C. Slowly sift in Carbopol 941 under propeller agitation and continue mixing for approximately 1 hour until completely hydrated.

(b) Cool to room temperature with slow agitation, adjust water to compensate for any evaporation.

(c) Add the molecular sieve particles and blend for approximately 2 hours until a smooth dispersion is obtained.

(d) Adjust pH of dispersion with 20% NaOH aqueous solution to a pH above 6.25. Blend with propeller agitation until local gelation is dissipated and mixture is completely smooth and fluid.

(e) Add denatured ethyl alcohol or hexylene glycol as required and blend further until dispersion is smooth and uniform.

The compositions of the Samples 14-17 are set forth in Table V below in terms of weight percent of the individual constituents.

TABLE V

| INGREDIENTS | Samples | | | |
|---|---|---|---|---|
| | 14 | 15 | 16 | 17 |
| CARBOPOL 941 | 0.8% | 0.8% | 0.8% | 0.8% |
| MOLECULAR SIEVE PARTICLES | 10.0 | 10.0 | 25.0 | 10.0 |
| WATER, DEIONIZED | 89.2 | 89.2 | 69.2 | 64.2 |
| HEXYLENE GLYCOL | — | — | 5.0 | — |
| DENATURED ETHYL ALCOHOL | — | — | — | 25.0 |

The formulations, except for Sample 17, for which no vial samples were prepared, were analyzed and stored for one month in the same manner as Samples 1-5. The The compositions of the present invention are useful in essentially all situations wherein topical application of the molecular sieve particles are desired. When the compositions are utilized as deodorants they can be applied as sprays, as semi-solid sticks, as lotions or as creams. Tests have established that the odor reducing capabilities of high-silica molecular sieves are not appreciably altered, if at all, by virtue of being applied to the odor source in the form of the compositions of the present invention. To illustrate this fact experiments were performed using the same molecular sieve adsorbent particles as in Examples 1-17 above and using triethylamine as the test adsorbate. In the experiments 22 ml. crimp cap vials equipped with Teflon-lined butyl rubber septa were used. The measured capacity of the vials was 22.5 ± 0 1 ml. The weighed adsorbent samples were placed in the vials. Thereafter the liquid adsorbate was added to the vials with a Hamilton syringe, and the vials were capped. Samples were shaken by hand to mix the liquid/solid/vapor phases and the vapors in the headspace of the vials analyzed by gas chromatography, after weighing and mixing, to measure the concentration of odor components in the headspace of the sample vials. The column was a fused silica adsorbent capillary, 0.53 mm. I.D. × 30 meters, containing a 1 micron internal coating of Carbowax as the adsorbent. A flame ionization detector was utilized to determine retention times. The oven conditions were 100.C isothermal. The particular gas chromatograph employed was a Perkin-Elmer model Sigma 2000.

Two test adsorbent samples were employed. The samples were originally prepared as aqueous suspensions and then dried in an air convection oven at 50° C. Sample No. 1 contained 78.7 weight percent molecular sieve particles, 14.2 weight percent colloidal magnesium aluminum silicate and 7.1 weight percent sodium carboxymethyl ether of cellulose having a DP of 400 and a DS of 0.79, all on a dry basis. Sample No. 2 contained the same ingredients except that the molecular sieve particles constituted 90.3 weight percent of the overall sample on a dry basis. For control purpose a sample of pure dry molecular sieve particles was employed. The results are set forth in Table VII below:

TABLE VII

| Sample | TEA, μl at 35° C. | Mass of Sample, g. | Odor Removal, % | Headspace TEA, p/p. | TEA loading on Sample, wt. % |
|---|---|---|---|---|---|
| 1 | 15.0 | 0.25 | 99.99 | 0.001 | 4.356 |
|   | 20.0 | 0.25 | 98.92 | 0.011 | 5.748 |
|   | 30.0 | 0.25 | 85.32 | 0.220 | 7.512 |
| 2 | 15.0 | 0.25 | 99.99 | 0.001 | 4.355 |
|   | 20.0 | 0.25 | 99.99 | 0.001 | 5.805 |
|   | 30.0 | 0.25 | 90.45 | 0.145 | 7.922 |
| Control | 15.0 | 0.25 | 99.99 | 0.001 | 4.356 |
|   | 20.0 | 0.25 | 99.99 | 0.001 | 5.807 |
|   | 30.0 | 0.25 | 90.92 | 0.136 | 7.970 |

What is claimed is:

1. Composition suitable for eliminating organic odors by contact with the odor source which comprises a suspension of particles of crystalline molecular sieves in an aqueous medium comprising water, a colloidal magnesium silicate having the structure of smectite and an alkali metal salt of the carboxymethoxy ether of cellulose.

2. Composition according to claim 1 wherein the particles of crystalline molecular sieves are hydrophobic siliceous molecular sieves, have particle sizes in the range of 1.5 to 20 micrometers and are present in an amount of from about 1 to about 75 parts by weight on the basis that the molecular sieves are in the anhydrous state.

3. Composition according to claim 2 wherein the crystalline hydrophobic siliceous molecular sieve particles are present in an amount of from about 5 to about 50 parts by weight on the basis that the molecular sieves are in the anhydrous state.

4. Composition according to claim 3 wherein the hydrophobic crystalline siliceous molecular sieves have particles in the range of 1.5 to 6.0 micrometers.

5. Composition according to claim 1 wherein the colloidal magnesium silicate is a colloidal magnesium aluminum silicate.

6. Composition according to claim 5 wherein the alkali metal salt carboxymethoxy ether of cellulose is the sodium salt and has a DP of from 200 to 1000 and a DS of from 0.38 to 1.45.

7. Composition according to claim 5 wherein the colloidal magnesium aluminum silicate is present in an amount of from 0.45 to 2.5 parts by weight.

8. Composition according to claim 6 wherein the DS of the sodium carboxymethoxy ether of cellulose is within the range of 0.65 to 0.90.

9. Process for imparting particles of a hydrophobic crystalline siliceous molecular sieve to a surface which comprises incorporating said particle into an aqueous suspension having a composition according to claim 1, applying said suspension to said surface and removing the aqueous constituent by evaporation.

10. Process according to claim 8 wherein the surface to which the particles are applied is a fibrous surface.

11. Process for preparing a composition of claim 1 which comprises providing an aqueous medium, imparting to said aqueous medium a colloidal magnesium silicate having the structure of smectite and maintaining the resulting composition until the silicate is swelled and completely hydrated, adding an alkali metal salt of a carboxymethoxy ether of cellulose to the aqueous medium containing the silicate and maintaining the resultant composition until the ether is swelled and completely hydrated and thereafter adding the particles of molecular sieve.

* * * * *